United States Patent
Hotier et al.

(10) Patent No.: US 6,429,346 B2
(45) Date of Patent: Aug. 6, 2002

(54) SIMULTANEOUS PROCESS FOR SIMULATED MOVING-BED DISMUTATION AND SEPARATION OF TOLUENE INTO BENZENE AND XYLENES

(75) Inventors: Gérard Hotier, Rueil Malmaison; Hugues Dulot, Evry; Michel Bailly, Nancy; Karine Ragil, Rueil Malmaison, all of (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 09/832,872

(22) Filed: Apr. 12, 2001

(30) Foreign Application Priority Data

Apr. 12, 2000 (FR) .............................. 00 04741

(51) Int. Cl.[7] .............................. C07C 5/12; C07C 5/22; C07C 5/52; C07C 7/13
(52) U.S. Cl. ...................... 585/475; 585/470; 585/828
(58) Field of Search ................ 585/475, 470, 585/828

(56) References Cited

U.S. PATENT DOCUMENTS 5,877,373 A   3/1999   Zinnen et al. .............. 585/475

FOREIGN PATENT DOCUMENTS

FR    2 761 904    10/1999

Primary Examiner—Thuan D. Dang
(74) Attorney, Agent, or Firm—Millen, White, Zelano & Branigan, P.C.

(57) ABSTRACT

A simultaneous process for simulated moving-bed dismutation and separation of a toluene feedstock into benzene and xylenes in the presence of a hydrogen-rich desorbent in at least one adsorber-reactor (100) that contains beds of a solid and comprises at least three zones (23, 24, 25) is described. Vapor-phase or supercritical feedstock (1) is introduced at the inlet of a reaction and adsorption zone (25) (zone III), and a raffinate (15) that is high in benzene and desorbent is recovered at the outlet. Desorbent (5, 7) is introduced at the inlet of a desorption zone (23) (zone I), and an effluent from which is drawn off a portion (8) in the form of an extract that is high in xylenes and desorbent is recovered at the outlet. The other portion of the effluent of zone I is introduced at the inlet of a reaction and desorption zone (24) (zone II), and an effluent is recovered at the outlet that is sent back to the inlet of reaction and adsorption zone III. Each of the zones comprises at least one bed that contains an adsorbent that is adapted to separate benzene, toluene and xylenes, and a catalyst that is adapted to dismutate toluene into benzene and xylenes, whereby the adsorbent and the catalyst are in solid form.

22 Claims, 3 Drawing Sheets

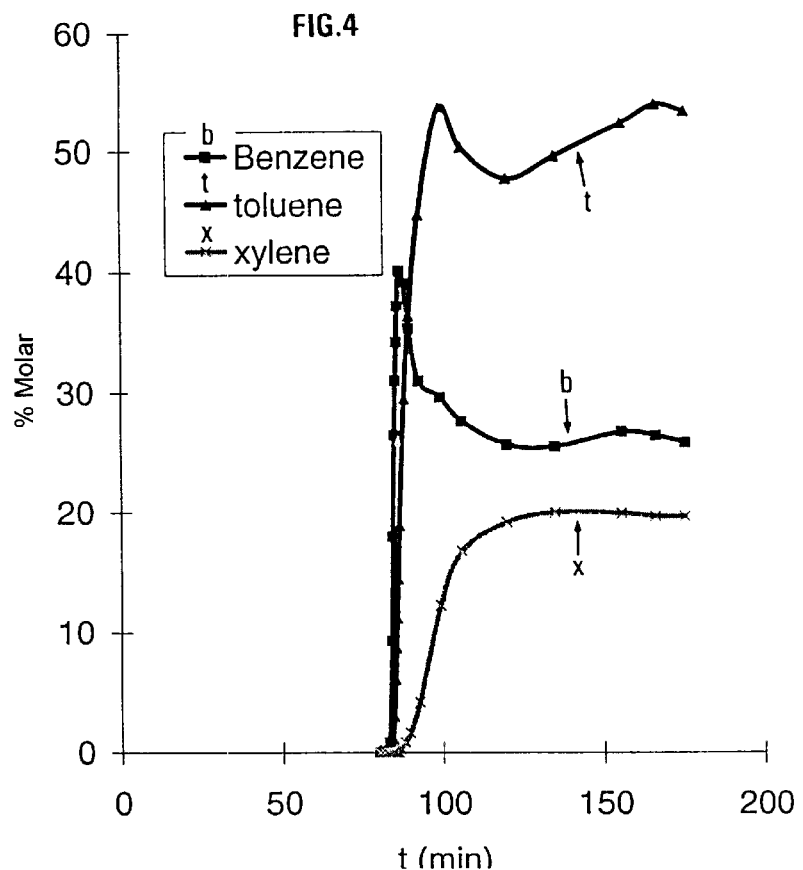
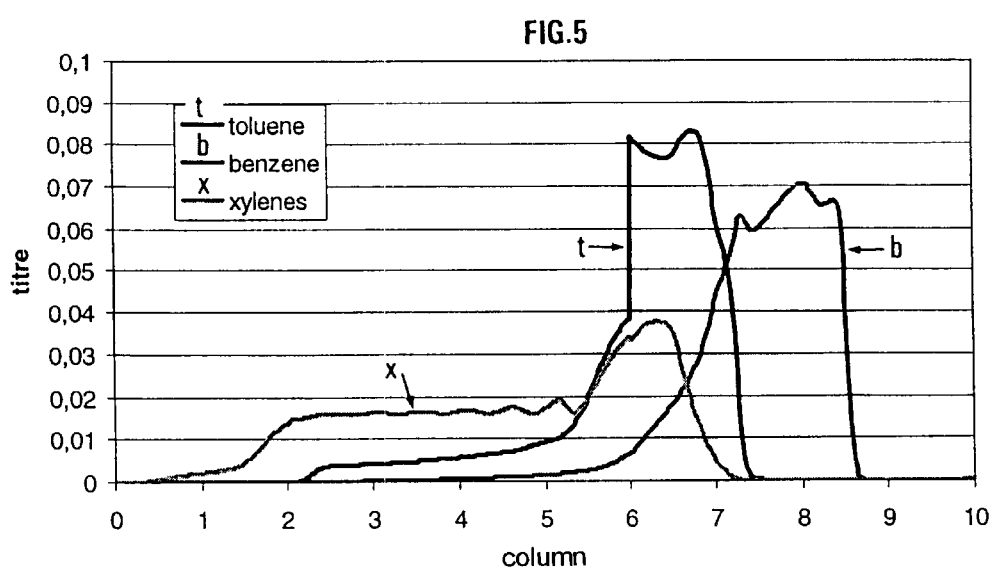

SIMULTANEOUS PROCESS FOR SIMULATED MOVING-BED DISMUTATION AND SEPARATION OF TOLUENE INTO BENZENE AND XYLENES

The invention relates to a process for the production of xylenes by adsorption-reaction in a simulated moving bed and particularly a simultaneous process for dismutation and separation of a toluene feedstock into benzene and xylenes.

Paraxylene is a raw material that makes it possible to synthesize terephthalic acid and toluene terephthalate that are then transformed into resins and fibers, such as, for example, Tergal. The most effective process for the production and purification of paraxylene in terms of productivity is the adsorption in a simulated moving bed or countercurrent that may or may not be combined with a final purification by crystallization and necessarily coupled to a catalytic isomerization on a zeolite, for example an EUO-structural-type zeolite that is mentioned, for example, in the French patent application of the applicant 99/07 968. The paraxylene is produced mixed with the other isomers into C8-aromatic compounds primarily by the processes of isomerization, reforming and dismutation of toluene.

The dismutation of toluene consists in using two toluene molecules to produce a benzene molecule and a xylene molecule. This dismutation is referred to as paraselective when the paraxylene constitutes the majority of the xylenes that are produced.

The non-selective reaction is catalyzed by MFI-type zeolites (or pentasil) or mordenite or else metals of group VIII; examples will be found in Patents FR 2761904, U.S. Pat. Nos. 4,007,231, 4,011,276, 4,029,716 and 4,052,476. In the case of the selective dismutation, the catalysts that are used are pentasils of type ZSM5, ZSM 11, ZSM22 or ZSM23 or ZSM 35 on which a deposit of outside material such as carbon (coke) or silicon was placed, as described in U.S. Pat. Nos. 4,260,843, 4,274,982, 4,380,685, 4,908,342, 5,173,461 and EP26962. The Mobil Oil Company uses two commercial processes for dismutation of toluene: the MTDP (non-selective) (see Oil & Gas Journal Vol. 69 No. 48, 1971 by Grandio et al.), and the MSTDP (selective) (see Oil & Gas Journal Vol. 90 No. 41, 1992 by Gora et al. or Europ. Chem. News Vol. 54, p. 1418, 1990). For these two processes, the major drawback is that the conversion of toluene is limited to 30% by the thermodynamic equilibrium. At the outlet of the reactor, the typical composition of the mixture is therefore benzene 15%, toluene 70%, and xylenes 15%. A series of two columns to be distilled is therefore necessary to separate these three products and to recycle the largest portion of the toluene to the inlet of the reactor. In the case of the paraselective process, among the isomers of the xylene, it is possible to obtain up to 90% of paraxylene, but if a compromise between the conversion of toluene and the paraselectivity is sought, the proportion of paraxylene is smaller (from 75 to 85%).

Since the 1970's, it has been known to use adsorption and reaction simultaneously (I&EC Fundam, 17 (1978) 1 D Sweich, J Villermaux). In the 1980's, it was proposed by Barker and Ganestsos to use the adsorption reaction in a simulated moving bed and in liquid phase, for example, for the inversion of saccharose and its total separation into glucose and fructose. Since the beginning of the 1990's, the idea of using adsorption and vapor-phase reaction simultaneously by using hydrogen as a vector fluid and as a reagent was first conceived by A. K. Ray and R. W. Carr (Chem Eng. Sci 50 (1995) n14, 2195–2202). It applied to the reaction for hydrogenation of mesitylene. Other authors adopted the idea of the separation reaction in a simulated moving bed and applied it to refining or to petrochemistry. It is thus possible to cite U.S. Pat. No. 5,530,173 that offers the additional original feature that the feedstock (mixture of aliphatic hydrocarbons with 6 to 8 carbon atoms) and the desorbent (normal pentane) are converted and separated simultaneously into isoparaffins with a high octane rating. Even more recently, U.S. Pat. No. 5,877,373 proposed the transalkylation of aromatic hydrocarbons into C9 and C10 by a mixture of toluene and benzene in a vapor phase and in the presence of hydrogen in such a way as to produce xylenes. In the latter document, it is not the implementation in a simulated moving bed but the circulation in opposite directions in the two reactors.

The object of the invention is the simultaneous production of benzene and xylenes by dismutation of toluene substantially without recycling toluene at the inlet of the reactor. To do this, the invention uses separation by adsorption, and the simultaneous reaction used in a simulated moving bed and in vapor phase.

More specifically, the invention relates to a simultaneous process for dismutation and separation of a feedstock that essentially consists of toluene, benzene and xylenes in the presence of a desorbent that is high in hydrogen in an adsorber-reactor that comprises at least three zones, characterized in that a) the vapor-phase or supercritical feedstock is introduced at the inlet of a reaction and adsorption zone (zone III), and at the outlet of said zone, a raffinate that is high in benzene and desorbent is recovered, b) the desorbent is introduced at the inlet of a desorption zone (zone I), and an effluent is recovered at the outlet of said zone from which a portion in the form of an extract that is high in xylenes and desorbent is drawn off, c) the other portion of the effluent of zone I is introduced at the inlet of a reaction and desorption zone (zone II), and an effluent that is sent to the inlet of reaction and adsorption zone III is recovered at the outlet of said zone.

The process is also characterized in that each of the zones comprises at least one bed that contains an adsorbent that is adapted to separate benzene, toluene and xylenes and a catalyst that is adapted to dismutate toluene into benzene and xylenes, whereby the adsorbent and the catalyst are in solid form.

When one of the zones comprises several beds, the latter comprises at least one bed that contains an adsorbent and a catalyst, whereby the remaining beds can contain either only a catalyst or only an adsorbent.

According to a variant of the invention, the catalyst can be a non-selective catalyst for paraxylene, adapted to obtain in the extract a mixture of xylenes that is close to the thermodynamic equilibrium.

It may be selected from the group that is formed by MFI zeolites or pentasils, mordenite in acid form or a precious metal of group VIIIB that is deposited on mordenite, or the Y zeolite that is exchanged with nickel, sodium, lanthanum or in acid form, the X zeolite that is exchanged with sodium, lanthanum or in acid form.

According to another variant of the invention, the catalyst is selective for the paraxylene and adapted to obtain a mixture of xylenes containing at least 80% of paraxylene.

These catalysts have very few active sites on their surface; they can be selected from the group of MFI zeolites, in particular ZSM5, ZSM11, ZSM22, ZSM23 that are made selective by deposition of coke, or silicon, or magnesium, or germanium or a combination of these elements at the surface of the zeolite.

With regard to the adsorbent, it may be selected from the group that is formed by silicalite, MFI zeolites or pentasils, faujasites (X or Y zeolites) that are exchanged by a cation of group IA or a cation of group IIA, or a cation of group IA and a cation of group IIA, the mordenites that are exchanged by a cation of group IA or a cation of group IIA, and the preceding zeolites made selective by deposition at the surface of carbon or magnesium or germanium or silicon or a combination of these elements.

According to a first variant, it is possible to use the same solid both as adsorbent and as catalyst in each bed.

According to a second variant, it is possible to produce an approximately homogenous mixture of adsorbent and catalyst in each of the beds in proportions of 95:5 to 5:95.

According to a third variant, it is possible to use a layer of catalyst and a layer of adsorbent in each bed in proportions of 95:5 to 5:95.

The operating conditions in the adsorber-reactor are generally as follows:

the temperature is between 220 and 520° C. and preferably between 275 and 350° C.

the H2/feedstock molar ratio is in, for example, proportions of 0.5/1 to 50/1 and preferably between 2/1 and 10/1 the total pressure in the adsorber-reactor is between atmospheric pressure and 400 bar and preferably between 1.5 and 40 bar (1 bar=$10^5$ Pa)

the partial pressure of hydrocarbons at the injection point of the feedstock is generally between 0.1 and 40 bar and preferably between 0.2 and 10 bar the volumetric flow rate is between a pph of 0.025 $h^{-1}$ and 25 $h^{-1}$, and preferably between 0.05 and 5 $h^{-1}$.

According to a first implementation of the process according to the invention that corresponds to a 3-zone adsorber-reactor, the fluid circulation between the last bed of zone III and the first bed of zone 1 can be interrupted with an all-or-nothing valve that is placed downstream from the sampling of the entire raffinate.

According to a second implementation of the process that corresponds to an adsorber-reactor with at least 4 zones, a recycling compressor that is located between the first bed and the last bed is adapted to control the flow of fluid that circulates successively in each of the zones.

According to a third implementation of the process that corresponds to an adsorber-reactor with at least four zones, the circulation of fluid between the last bed of zone IV and the first bed of zone I is interrupted with an all-or-nothing valve, and the fluid that contains the hydrogen that is obtained from zone IV is recovered and sent back to the intake of the hydrogen compressor that delivers this desorbent to the inlet of zone I.

The invention will be better understood from FIGS. 1 to 5 and their descriptions as well as with the examples for preparation of catalytic adsorbents and their implementation.

FIG. 4 shows the molar composition at the outlet of the absorption column.

FIG. 5 illustrates the stationary profile of composition based on the column number.

Figure 1:
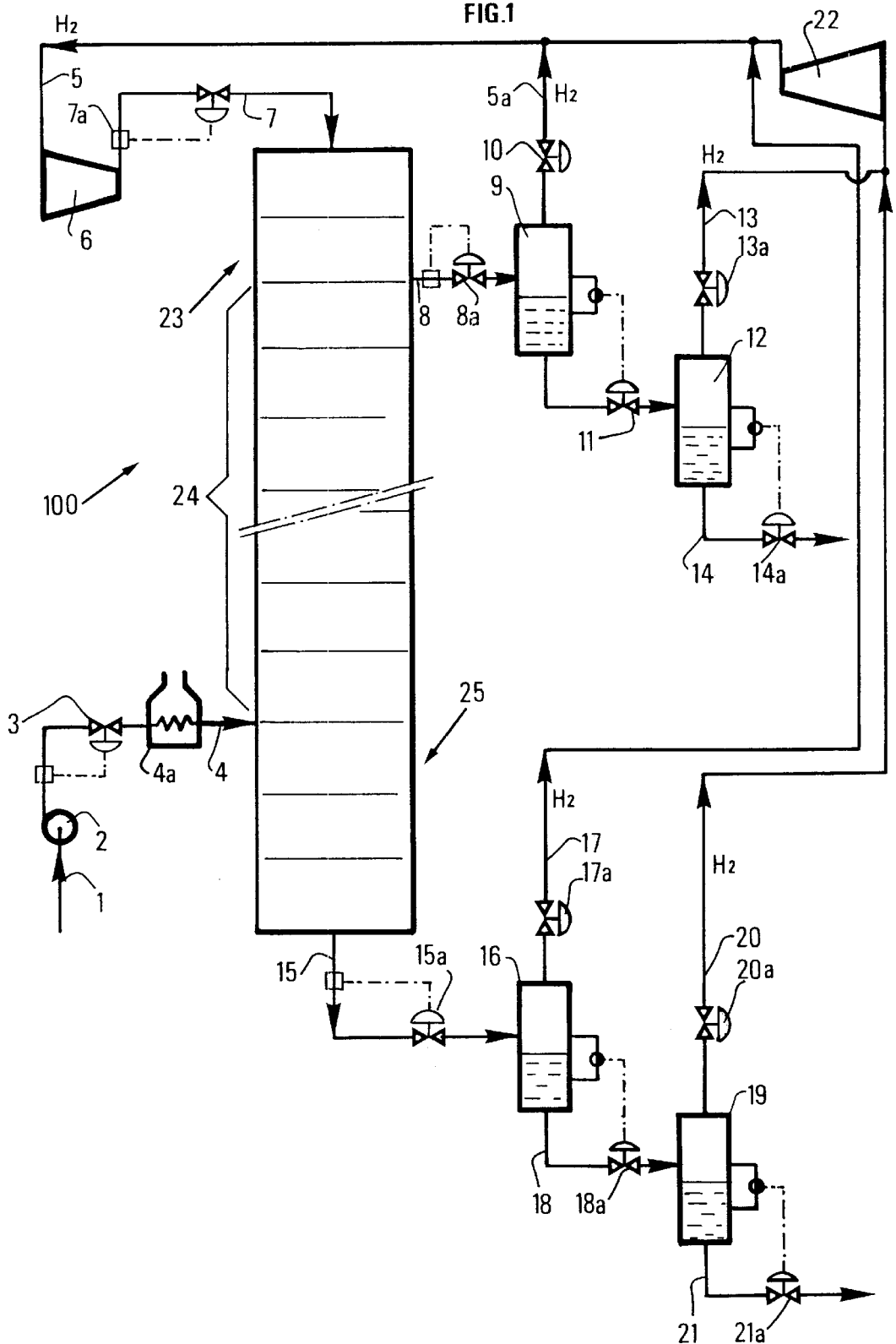
FIG. 1 depicts an entire adsorption reaction unit as well as its circuits for supply and draw-off.

A feedstock 1 that essentially consists of toluene is conveyed by a pump 2 at a flow rate that is controlled by regulating means 3 that consist of a control valve and a flowmeter. In a furnace 4a, said feedstock is vaporized before being sent via a line 4 to catalytic adsorbent beds that are contained in a reaction column 100 that operates in a simulated moving bed. A vector fluid 5 that essentially consists of hydrogen is compressed in a compressor 6 at a flow rate that is controlled by regulating means 7a that consist of a control valve and a flowmeter for being sent via a line 7 to the catalytic adsorbent beds. A set of means 8a that consists of a control valve and a flowmeter makes it possible to draw off via a line 8 an extract that essentially consists of hydrogen and xylenes from catalytic adsorbent beds. This mixture is flashed in a high-pressure separator 9 whose pressure is regulated with a valve 10. A hydrogen-rich gaseous effluent (line 5a) is recycled to the inlet of vector fluid 5. The liquid level in separator 9 is regulated by a level control valve 11. This liquid is flashed in a low-pressure separator 12 whose pressure is regulated with a valve 13a. A hydrogen-rich gaseous effluent (line 13) is recycled to the intake of a compressor 22 that raises the level of pressure and sends this flow back via line 5 to the intake of compressor 6. The liquid level in separator 12 is regulated by a level control valve 14a. The liquid that exits the low-pressure separator via a line 14 consists for the most part of xylenes (mixture of three isomers with a non-paraselective catalyst, paraxylene essentially with a paraselective catalyst). A unit 15a that consists of a control valve and a pressure sensor makes it possible to draw off via a line 15 raffinate that essentially consists of hydrogen and benzene from catalytic adsorbent beds. This mixture is flashed into a high-pressure separator 16 whose pressure is regulated with a valve 17a; a hydrogen-rich gaseous effluent is recycled via a line 17 to the inlet of vector fluid 5. The liquid level in separator 16 is regulated by a level control valve 18a that is placed on an outlet line 18 for this liquid. This liquid is flashed into a low-pressure separator 19 whose pressure is regulated with a valve 20a. A hydrogen-rich gaseous effluent is recycled via a line 20 to the intake of compressor 22 that raises the pressure level and sends back this flow to the intake of compressor 6. An addition of fresh hydrogen can be introduced into line 20 upstream from compressor 22. The liquid level in separator 19 is regulated by a level control valve 21a that is placed on an outlet line 21 of the raffinate. The liquid that exits from low-pressure separator 19 consists for the most part of benzene. The catalytic adsorbent is placed in a series of 9 beds that are placed in a closed loop. At 23, the diagram of FIG. 1 depicts zone 1 that consists of two beds and is delimited by the injection of vector fluid that essentially consists of hydrogen and the sampling of extract that consists of hydrogen and xylenes; reference mark 24 corresponds to zone 2 that consists of 4 beds and is delimited by the sampling of extract and the injection of feedstock that essentially consists of toluene; and reference mark 25 corresponds to zone 3 that consists of three beds and is delimited by the injection of toluene and the sampling of raffinate that essentially consists of benzene and hydrogen. Contrary to what takes place at the joining of zones 1 and 2 and that of zones 2 and 3, no fluid passes between zones 1 and 3 because an all-or-nothing valve or a nonreturn valve prevents the fluids from circulating between these two beds.

Figure 2:
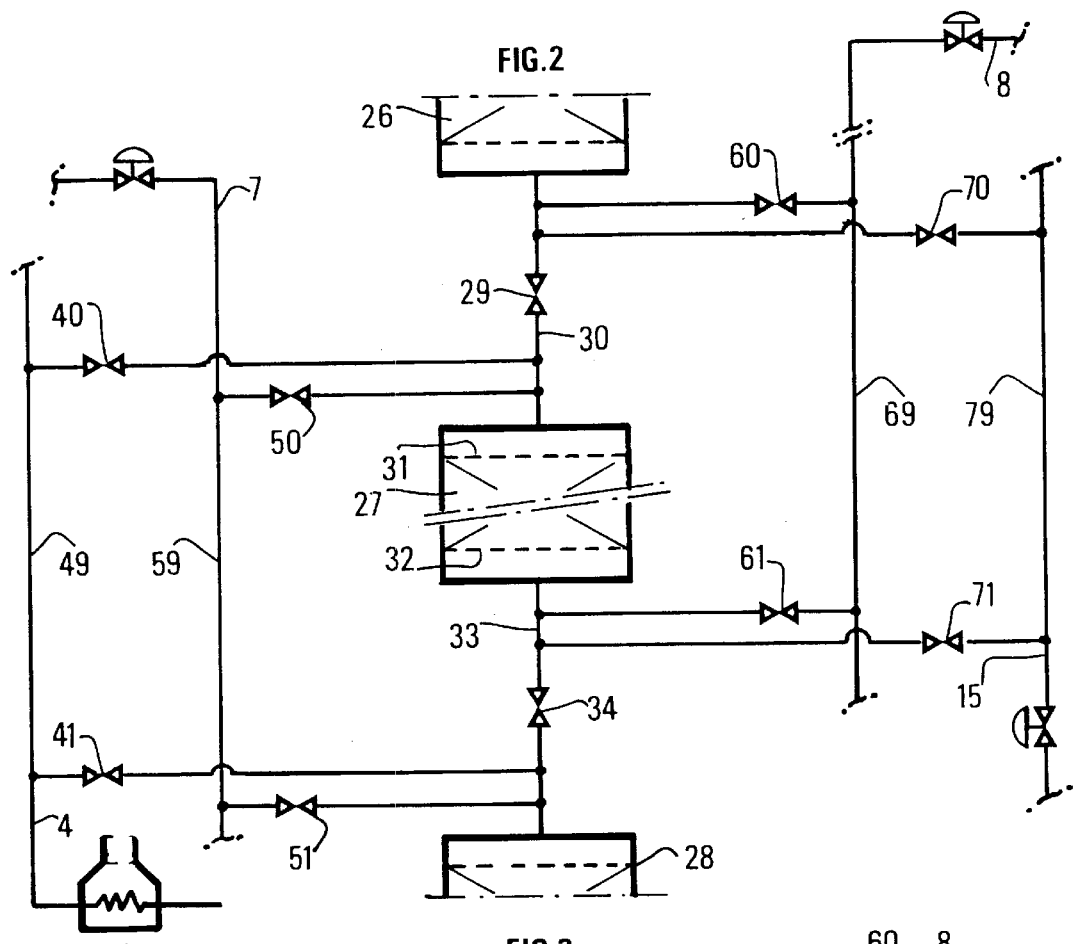
FIGS. 2 and 3 depict two variants of connecting supply and draw-off fluids around a catalytic adsorbent bed.
Figure 3:
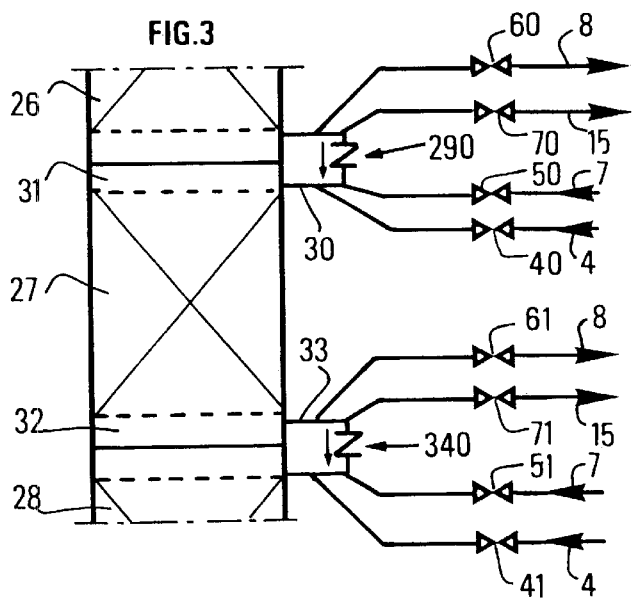

Three successive beds 26, 27 and 28 of catalytic adsorbent are depicted in FIGS. 2 and 3. In a first variant (FIG. 2), each of the beds is placed in an individualized reactor. In a second variant (FIG. 3), each of the beds is placed in successive compartments that are isolated from one another in the same reactor.

The unit that is placed around one bed consists successively of an all-or-nothing valve 29 (FIG. 2) or a nonreturn valve 290 (FIG. 3), whose object is to ensure a unidirectional flow from bed 26 to bed 27 in all situations. The point of peak pressure is located in the hydrogen injection (beginning of zone 1) and the point of minimum pressure is located in the raffinate draw-off (end of zone 3). A particular case occurs during the stage of the cycle when valves 70 and 50 that are connected respectively to raffinate draw-off line 15 and to desorbent inlet line 7 are opened simultaneously: the closing of valve 29 (FIG. 2) is then controlled to prevent the hydrogen that is injected through valve 50 from flowing directly to valve 70 via a line 30 that connects two beds 26 and 27 without passing through the catalytic adsorbent beds. In the case of FIG. 3, nonreturn valve 290 assumes a similar function: it closes since the pressure at the outlet of valve 50 is stronger than that at the inlet of valve 70. In all of the other stages of the cycle, valve 29 or nonreturn valve 290 is open, and the gas circulates from bed 26 to bed 27. Downstream from valve 29 or nonreturn valve 290, line 30 to which are connected the feedstock injection lines (controlled by an all-or-nothing valve 40) and hydrogen injection (controlled by an all-or-nothing valve 50) are found. The fluid then returns into the reactor (FIG. 2) or the reactor compartment (FIG. 3) that contains catalytic adsorbent bed 27. This bed is kept in place by means 31 and 32 that also ensure the distribution of gas throughout the section. These means that are known to one skilled in the art consist of, for example, grids or inert balls. The gas then comes out from bed 27 via a line 33. Connected to line 33 are extract draw-off lines 8 (controlled by an all-or-nothing valve 61) and raffinate draw-off lines 15 (controlled by an all-or-nothing valve 71). Downstream from these two connections, an all-or-nothing valve 34 (FIG. 2) or a nonreturn valve (340) (FIG. 3) whose object is to ensure a unidirectional flow from bed 27 to bed 28 in all situations is found.

The injection of the feedstock (toluene) in each of the beds comprises a common part already described in FIG. 1, downstream from furnace 4a, the toluene circulates in a line 49 to which are connected valves 40, 41, . . . serving each of the nine catalytic adsorbent beds. The injection of the vector fluid (hydrogen) in each of the beds comprises a common part that is already described in FIG. 1. Downstream from control valve 7a, the hydrogen circulates in a line 59 to which are connected valves 50, 51, . . . serving each of the nine catalytic adsorbent beds. The extract draw-off (hydrogen-xylenes mixture) from each of the beds comprises a common part that is already described in FIG. 1. Upstream from control valve 8a, the extract circulates in a line 69 to which are connected valves 60, 61, . . . serving each of the nine catalytic adsorbent beds. The raffinate draw-off (hydrogen-benzene mixture) from each of the beds comprises a common part that is already described in FIG. 1. Upstream from control valve 15a, the extract circulates in a line 79 to which are connected valves 70, 71, . . . serving each of the nine catalytic adsorbent beds. According to the principle of the simultaneous countercurrent, the injection points and the sampling points of different fluids as well as the point of isolation between zones 1 and 3 are passed periodically in the direction of the circulation of the gas. The operation of the unit will be better understood by describing the positions of valves around bed 27 during each of the nine periods of the cycle. For each of the other eight beds, the sequencing consists of a circular permutation of nine periods.

Period 1: Bed 27 in zone 3; sampling of raffinate at the outlet of bed 27; valves 40, 50, and 61 are closed, valve 71 is open, valve 29 is open, valve 34 is closed (FIG. 2); nonreturn valve 290 is open; nonreturn valve 340 closes by pressure difference (FIG. 3).

Period 2: Bed 27 in zone 3; valves 40, 50, 61 and 71 are closed; valves 29 and 34 are open (FIG. 2); nonreturn valves 290 and 340 are open.

Period 3: Bed 27 in zone 3; injection of feedstock at the inlet of bed 27; valves 50, 61 and 71 are closed, valve 71 is open, valves 29 and 34 are open (FIG. 2), nonreturn valves 290 and 340 are open.

Period 4: Bed 27 in zone 2; valves 40, 50, 61 and 71 are closed; valves 29 and 34 are open (FIG. 2); nonreturn valves 290 and 340 are open.

Period 5: Bed 27 in zone 2; valves 40, 50, 61 and 71 are closed; valves 29 and 34 are open (FIG. 2); nonreturn valves 290 and 340 are open.

Period 6: Bed 27 in zone 2; valves 40, 50, 61 and 71 are closed, valves 29 and 34 are open (FIG. 2), nonreturn valves 290 and 340 are open.

Period 7: Bed 27 in zone 2; valves 40, 50, 61 and 71 are closed; valves 29 and 34 are open (FIG. 2), nonreturn valves 290 and 340 are open.

Period 8: Bed 27 in zone 1; sampling of extract at the outlet of bed 27; valves 40, 50 and 71 are closed; valve 61 is open; valves 29 and 34 are open (FIG. 2), nonreturn valves 290 and 340 are open.

Period 9: Bed 27 in zone 1; injection of vector fluid at the inlet of bed 27; valves 40, 61 and 71 are closed; valve 50 is open; valve 29 is closed; valve 34 is open (FIG. 2), nonreturn valve 290 closes by pressure difference; nonreturn valve 340 is open (FIG. 3).

FIGS. 1 and 2 refer to a three-zone simulated moving bed that is well adapted to a process where the vector fluid (hydrogen) and the effluents (benzene and xylenes) flash-separate very easily. It is possible, however, to choose to operate with four zones. The fourth zone is then located between the sampling of raffinate and the vector fluid injection. The advantage of operating with four zones is to no longer have need of valves 29 and 34 or nonreturn valves 290; a compressor that is inserted between the first and last bed makes it possible to drive the gas flow that circulates through the beds and to take the same direction always. This compressor, however, is to be equipped with a volumetric flow control in such a way that it will successively assume the four separate flow rate values of the four zones: reference will be made to, for example, U.S. Pat. No. 5,284,992 of the applicant that exhibits this technique in the case of a circulation of liquid. As an alternative, if the compressor is operated at a constant flow rate with desynchronized periods, reference will be made to U.S. Pat. No. 5,578,215 of the applicant for more details. Finally, if more details on the practical use of the simulated moving bed in vapor phase with an additional control of operating pressures zone by zone are desired, reference is to be made to WO 93/22022 of the applicant.

The catalytic adsorbent can be one and the same solid that simultaneously exhibits suitable adsorption properties (adequate capacity and selectivity: the components absolutely having to be eluted in the order of benzene and then toluene and xylenes) and suitable catalysis properties: catalysis of the dismutation reaction and, if possible, not catalysis of the xylene isomerization reaction.

Examples 1 to 4 describe the preparation and the implementation of a particular solid; a ZSM5 that is treated by deposition of external silica.

Such a solid operates under rigid temperature conditions: at 325° C., all of the required properties are obtained simultaneously. If the temperature is too low, the conversion is much too low at 280° C.; if the temperature is too high at 375° C., for example, the selectivity is much too low. The conditions of volumetric flow rate, flow rate and partial pressure of toluene at the point of entry of the feedstock are also optimal in limited-value slots.

It is also possible to use two separate solids in the same bed mixed in a homogeneous manner or placed in different layers:

One having catalysis properties: all of the catalysts known for dismutation of toluene or more generally for transalkylation are therefore potential candidates with the exception of the catalysts based on noble metals that catalyze the hydrogenation of aromatic compounds since this reaction is strongly exothermic.

The other having adsorption properties: the MFI-structural-type zeolites seem the best adapted, however, for example, one of the silicalites under study which has an Si/Al ratio=600 exhibits selectivity inversion.

EXAMPLE 1

The initial material is the ZSM-5 zeolite which has an Si/Al ratio of about 37. This zeolite is then extruded with silica, then dried and calcined under dry air in such a way as to have 70% zeolite and 30% silica. About 145 g of these extrudates (Si/Al ratio of about 51, size 12–16 mesh) that is impregnated by a mixture of heptane and 31.4 g of polysiloxane, while being stirred constantly for 2 hours at ambient temperature, is considered.

After vacuum evaporation of the solvent (40° C. and 100 Pa) and drying under nitrogen (200° C.), the extrudates are calcined under air for 4 hours at 550° C. About 155 g of treated extrudates is recovered, and the Si/Al ratio is about 52.5.

EXAMPLE 2

The initial material is the same ZSM-5 zeolite which has an Si/Al ratio of about 37. About 170 g of dry ZSM-5 zeolite powder is weighed, and the latter is impregnated by a mixture of heptane and 55.8 g of polysiloxane. The slurry that is obtained is stirred for 2 hours at ambient temperature.

After vacuum evaporation of the solvent (40° C. and 100 Pa) and drying under nitrogen (250° C.), the powder is calcined for 4 hours at 550° C. 150 g of this powder is used to form extrudates with silica in such a way as to have 60% of treated ZSM-5 crystals and 40% of silica (size 12–16 mesh).

EXAMPLE 3 (FIG. 4)

A column of about 80 cm and with a 16 mm diameter filled with extrudates manufactured in Example 2 is considered. The pure hydrogen is circulated in the column, then a mixture of toluene and hydrogen is returned to this column, and the composition of the effluents of this column is observed.

Here, a temperature of 325° C., a total pressure of 10 bar, a partial pressure of 1.1 bar of toluene and a total flow rate at the inlet of 3.75 nL.h$^{-1}$ are considered.

FIG. 4 shows the molar composition at the outlet of the column. At the outlet of the column, a benzene front followed by a toluene front and finally a xylene front are clearly observed. This catalytic adsorbent therefore has the properties that allow it to convert toluene and a selectivity relative to the reagent and products. It is therefore suitable for being used in a simulated moving bed.

EXAMPLE 4 (FIG. 5)

This example shows that it is possible to convert the toluene totally into benzene and xylenes.

The assembly in a simulated moving bed with 4 zones of respectively 2-4-2-2 beds of 0.5 m of length and 16 mm of diameter, filled with extrudates of Example 1, is considered. 6.13 n L.h−1 is returned to this simulated moving bed by hydrogen desorption, and 0.13 n L.h−1 is returned to supply pure toluene. By operating at 325° C. and 10 bar, respectively 7.79; 2.43; 2.56 and 1.61 nL.h−1 and a switching time of 1600 s are obtained with flow rates in the four zones; the stationary composition profile is depicted in FIG. 5.

The raffinate that is sampled at the outlet of column 8 (0.95 n/h) consists of 6.85% of benzene in hydrogen, and the extract sampled at the outlet of column 2 (5.56 nl/h) consists of 1.17% of xylenes in hydrogen.

What is claimed is:

1. A simultaneous process for simulated moving-bed dismutation of a feedstock comprising primarily toluene and separation of toluene, benzene and xylenes in the presence of a desorbent consisting essentially of hydrogen in at least one adsorber-reactor containing a plurality of beds of a solid and comprising at least three zones, wherein
   a) a vapor-phase or supercritical feedstock is introduced at the inlet of a reaction and adsorption zone (zone III), and at the outlet of said zone, a raffinate enriched in benzene and desorbent is recovered,
   b) the resultant desorbent is introduced at the inlet of a desorption zone (zone I), and an effluent is recovered at the outlet of said zone from which a portion in the form of an extract enriched in xylenes and desorbent is drawn off,
   c) another portion of the effluent of zone I is introduced at the inlet of a reaction and desorption zone (zone II), and an effluent that is sent to the inlet of reaction and adsorption zone III is recovered at the outlet of said zone;
   wherein each of the zones comprises at least one bed that contains an adsorbent adapted to separate benzene, toluene and xylenes and a catalyst adapted to dismutate the toluene into benzene and xylenes, the adsorbent and the catalyst being in solid form.

2. A process according to claim 1, wherein the catalyst is a non-selective catalyst for paraxylene, adapted to obtain in the extract a mixture of xylenes proximate to thermodynamic equilibrium.

3. A process according to claim 1, wherein the catalyst is selected from the group consisting of MFI zeolites and pentasils, mordenite in acid form, the mordenite containing a deposited precious metal of group VIIIB, a Y zeolite exchanged with nickel, sodium, or lanthanum, or in acid form, and an X zeolite exchanged with sodium or lanthanum, or in acid form.

4. A process according to claim 1, wherein the catalyst is a selective catalyst for paraxylene, adapted to obtain a mixture of xylenes that contains at least 80% of paraxylene.

5. A process according to claim 1, wherein the catalyst is selected from the group consisting of MFI zeolites, ZSM5, ZSM11, ZSM22, ZSM23, made selective by deposition of carbon, or silicon, or magnesium, or germanium or a combination of these elements on the surface of the zeolite.

6. A process according to claim 1, wherein the adsorbent is selected from the group consisting of silicalite, MFI zeolites or pentasils, faujasites (X or Y zeolites) exchanged by a cation of group IA or a cation of group IIA, or a cation of group IA and a cation of group IIA, mordenites exchanged by a cation of group IA or a cation of group IIA, said zeolites being made selective by a deposition on the surface of carbon or magnesium or germanium or silicon or a combination of these elements.

7. A process according to claim 1, wherein the same solid is used both as adsorbent and as catalyst in each bed.

8. A process according to claim 1, wherein an approximately homogeneous mixture of adsorbent and catalyst is provided in each of the beds in proportions of 95:5 to 5:95.

9. A process according to claim 1, wherein a layer of catalyst and a layer of adsorbent are used in each bed in proportions of 95:5 to 5:95.

10. A process according to claim 1, wherein the temperature is between 220 and 520° C.

11. A process according to claim 1, wherein the H2/feedstock molar ratio is between 0.5/1 and 50/1.

12. A process according to claim 1 conducted at a total pressure between atmospheric pressure and 400 bar.

13. A process according to claim 12, wherein the partial pressure of hydrocarbons is between 0.1 and 40 bar.

14. A process according to claim 1 conducted at a volumetric flow rate of 0.025 to 25 $h^{-1}$.

15. A process according to claim 1 conducted in an adsorber-reactor having three zones in which the fluid circulation between the last bed of zone III and the first bed of zone I is interrupted with an all-or-nothing valve placed downstream from sampling of the entire raffinate.

16. A process according to claim 1 conducted in an adsorber-reactor with at least four zones and wherein a recycling compressor located between the first and the last bed adjusts the flow rate of fluid circulating successively into each of the zones.

17. A process according to claim 1 conducted in an adsorber-reactor with at least four zones in which fluid circulating between the last bed of zone IV and the first bed of zone I is interrupted with an all-or-nothing valve and in which a fluid that contains the hydrogen obtained from zone IV is recovered and sent back to the inlet of zone 1.

18. A process according to claim 10 wherein the temperature is between 275° C. and 350° C.

19. A process according to claim 11 wherein said molar ratio is between 2/1 and 10/1.

20. A process according to claim 12 wherein the total pressure is between 1.5 and 40 bar.

21. A process according to claim 13 wherein said partial pressure is between 0.2 and 10 bar.

22. A process according to claim 14 wherein the volumetric flow rate is between 0.05 and 5 $h^{-1}$.

* * * * *

UNITED STATES PATENT AND TRADEMARK OFFICE
CERTIFICATE OF CORRECTION

PATENT NO. : 6,429,346 B2
DATED : August 6, 2002
INVENTOR(S) : Gerard Hotier et al.

It is certified that error appears in the above-identified patent and that said Letters Patent is hereby corrected as shown below:

<u>Column 8,</u>
Line 23, change "raffmate" to -- raffinate --.

Signed and Sealed this

Twenty-first Day of June, 2005

JON W. DUDAS
*Director of the United States Patent and Trademark Office*